(12) United States Patent
Wöhrle et al.

(10) Patent No.: US 6,566,562 B2
(45) Date of Patent: May 20, 2003

(54) PROCESS FOR THE PREPARATION OF ISOLONGIFOLANOL

(75) Inventors: Ingo Wöhrle, Holzminden (DE); Jürgen Nienhaus, Holzminden (DE)

(73) Assignee: Haarmann & Reimer GmbH (DE)

( * ) Notice: Subject to any disclaimer, the term of this patent is extended or adjusted under 35 U.S.C. 154(b) by 0 days.

(21) Appl. No.: 10/014,046

(22) Filed: Dec. 11, 2001

(65) Prior Publication Data

US 2002/0111519 A1 Aug. 15, 2002

(30) Foreign Application Priority Data

Dec. 14, 2000 (DE) .......................... 100 62 418
Feb. 12, 2001 (DE) .......................... 101 06 421

(51) Int. Cl.$^7$ ............................................. C07C 35/22
(52) U.S. Cl. .......................................... 568/817; 512/19
(58) Field of Search .......................... 568/817; 512/19

(56) References Cited

U.S. PATENT DOCUMENTS

| | | | | |
|---|---|---|---|---|
| 4,000,202 A | * | 12/1976 | Maupetit | |
| 4,229,323 A | * | 10/1980 | Teisseire | |
| 4,277,631 A | * | 7/1981 | Oppolzer | |
| 4,439,354 A | * | 3/1984 | Light | |
| 5,693,606 A | * | 12/1997 | Brunke | |
| 2002/0040167 A1 | | 4/2002 | Pickenhangen et al. | ..... 568/667 |

OTHER PUBLICATIONS

Chemical Abstracts, vol. 89, No. 7, Aug. 14, 1978 Columbus, Ohio, US; abstract No. 59977q, XP002186534 *Zusammenfassung* *idem* & JP 78 034763 A (Takasago Perfumery Co Ltd).

H. Kropf et al: Houben–Weyl; Methoden der Organischen Chemie; Band VI/1a, Teil 1 1979, Georg Thieme Verlag, Stuttgart, DE XP002186533 *Seite 425—Seite 430*.
J. Agri. Food Chem., (month unavailable) 1994, 42, pp. 138–142, Isabelle Bombarda, Jacqueline Smadja, Emile M. Gaydou, Jacques–Yves Conan and Robert Faure, Structure Elecidation of Oxidation–Reduction Products of Isolongifolene.
Tetrahedron Lett. 8, (month unavailable) 1964, pp. 417–427, J.R. Prahlad, R. Ranganathan, U. Ramdas Nayak, T.S. Santhanakrishnan and Sukh Dev.
J. Org. Chem. 35, (month unavailablel) 1970 pp. 1172–1173, L.K. Lala and J.B. Hall, Products Of the Action of Peracetic Acid on Isolongifolene.
Helv. Chim. Acta. 50, (month unavailable) 1967, pp. 153–165, von K. H. Schulte–Elte and G. Ohloff, Über eine aussergewöhnliche Stereospezifität bei der Hydroborierung der diastereomeren (1R)–Isopulegole mit Diboran.
Synthesis (month unavailable) 1972, pp. 194–195, M.N. Sheng, Base–Catalyzed Isomerization of Epoxides. II Preparation of 3–Hydroxcyclooctene from Cyclooctenen Oxide
Tetrahedron 39 (month unavailable) 1983, pp. 2323–2367, A.S. Rao, Recent Advances in the Preparation and Synthetic Application of Oxiranes.
Comprehensive Organic Transformations, Richard C. Larock, (month unavailable) 1989, pp. 117–118, Isomerization of Alkenes.
Abstract of JP 83–22450 (Sep. 1983).

* cited by examiner

*Primary Examiner*—Michael L. Shippen
(74) *Attorney, Agent, or Firm*—Pendorf & Cutliff

(57) ABSTRACT

The invention relates to the preparation of the compounds isolongifolanol (IUPAC name: 2,2,7,7-tetramethyltricyclo [6.2.1.0$^{1,6}$]undecan-6-ol) and isolongifolenol (IUPAC name: 2,2,7,7-tetramethyltricyclo[6.2.1.0$^{1,6}$]undec4-en-6-ol) and to the use thereof as fragrance or aroma substance.

7 Claims, No Drawings

PROCESS FOR THE PREPARATION OF ISOLONGIFOLANOL

FIELD OF THE INVENTION

The invention relates to the preparation of the compounds isolongifolanol (IUPAC name: 2,2,7,7-tetramethyltricyclo[6.2.1.0$^{1,6}$]undecan-6-ol) and isolongifolenol (1,3,4,5,6,8a-hexahydro-1,1,5,5-tetramethyl-2,4a-methanonaphthalen-8a (2H)-ol; IUPAC name: 2,2,7,7-tetramethyltricyclo[6.2.1.0$^{1,6}$]undec-4-en-6-ol), and to the use thereof as fragrances or aroma substances in functional perfumery and in fine perfumery.

BACKGROUND OF THE INVENTION

There is a constant need for new fragrances with interesting scent notes, particularly for those having an additional use. This need arises from the need to adapt to changing trends and fashions and the associated need to supplement the existing palette of natural fragrances. Furthermore, there is, in general, a constant need for synthetic fragrances which can be prepared favorably and with uniform quality. These substances should have odor profiles which are as pleasant and as natural as possible.

Because of the highly fluctuating prices and qualities of natural patchouli oils there is an urgent need for synthetic compounds with patchouli character and woody-earthy notes which can be prepared in an efficient synthesis from cost-effective starting materials and, moreover, broaden the composition possibilities of the perfumer with their original scent properties.

Isolongifolanol (4) is known from JP 58/022450 B4 and JP 60/010007 B4. However, the compound is obtained in the process described therein only with a content of 5% by hydrogenation of the isolongifolene oxide (2) in a multi-component mixture.

J. Agric. Food. Chem. 1994, 42, 138–142 describes the reaction of isolongifolene oxide (2) with lithium aluminum hydride. In this way, small amounts (<100 mg) of the isolongifolanol (4) were obtained with a yield of 76%. Disadvantages of this process are the price of the reducing agent and the safety problems associated with the handling of lithium aluminum hydride.

SUMMARY OF THE INVENTION

It was, therefore, also the object to prepare compound 4 in an efficient, reliable synthesis which can be realized on an industrial scale, from cost-effective starting materials.

The invention therefore provides a process for the preparation of isolongifolanol (4), characterized by the following process steps:

a) epoxidation of isolongifolene (1) to give isolongifolene oxide (2), b) rearrangement of isolongifolene oxide (2) in the presence of a base to give isolongifolenol (3) and c) reduction of isolongifolenol (3) to give isolongifolanol (4).

DETAILED DESCRIPTION OF THE INVENTION

The following equation can illustrate the invention:

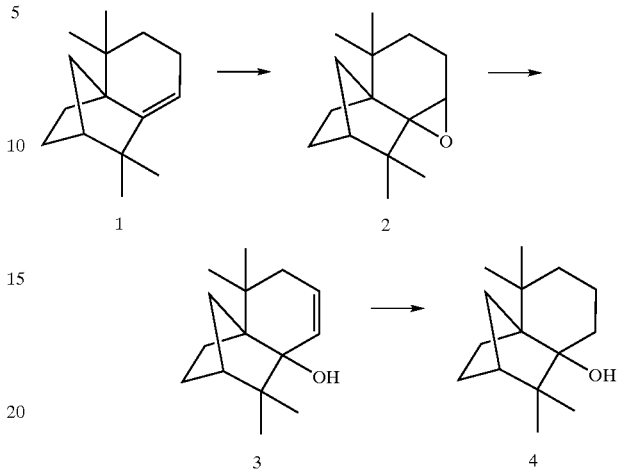

In the first stage, isolongifolene (1) can be reacted in a known manner, for example with peracetic acid, to give isolongifolene oxide (2) (Tetrahedron Lett. 1964, 8, 417; J. Org. Chem. 1970, 35, 1172).

In the second step, the epoxide 2 can be rearranged in thermally and chemically inert solvents in the presence of a strong base to give isolongifolenol (3).

Conditions under which the rearrangement can be carried out favorably are given, for example, in Helv. Chim. Acta 1967, 50, 153; Synthesis 1972,194 and also Tetrahedron 1983, 39, 2323. An overview is given in Larock, Comprehensive Organic Transformations, VCH, 1989, 117–118.

Strong bases are typically alkali metal, alkaline earth metal and light metal alkoxides or alkali metal, alkaline earth metal and light metal amides.

For the purposes of this invention, light metals are, in particular, aluminum, titanium and beryllium.

It is particularly surprising that the rearrangement with unbranched metal alkoxides such as methoxides and ethoxides leads to the isolongifolenol with very high selectivity. Using these bases, epoxides typically produce the corresponding vicinal hydroxyalkyl ethers (Chem. Rev.1959, 737).

Examples of bases which may be mentioned are lithium diethylamide, lithium n-dipropylamide, lithium diisopropylamide, lithium n-dibutylamide, lithium ethylenediamide, trilithium phosphate, sodium hydride, potassium hydride, diethylaluminum 2,2,6,6-tetramethylpiperidide, potassium tert-butoxide, sodium tert-butoxide, lithium tert-butoxide, sodium ethoxide, potassium ethoxide, lithium ethoxide, sodium methoxide, potassium methoxide, lithium methoxide, sodium isopropoxide, potassium isopropoxide, lithium isopropoxide, magnesium ethoxide, magnesium methoxide, calcium ethoxide and calcium methoxide.

Preferred bases are the alkoxides of lithium, sodium and potassium having 1 to 6 carbon atoms.

More preference is given to sodium methoxide, sodium ethoxide, sodium isopropoxide, sodium tert-butoxide, potassium methoxide, potassium ethoxide, potassium isopropoxide, potassium tert-butoxide, lithium methoxide, lithium ethoxide, lithium isopropoxide and lithium tert-butoxide.

0.3 to 2.5 molar equivalents of the base, preferably 0.6 to 1.8 equivalents and more preferably 0.8 to 1.4 equivalents are used. The equivalents here are based on the content of epoxide 2.

The reaction can be carried out in a large number of solvents. Suitable are, in general, nonpolar or aprotically polar solvents.

Solvents which may be mentioned are open-chain or cyclic dialkyl or alkyl aryl ethers, such as, for example: diethyl ether, tetrahydrofuran, anisole, aliphatic or aromatic hydrocarbons having 6 to 10 carbon atoms, such as cyclohexane, n-heptane, isooctane, toluene, ethylbenzene, xylenes, open-chain or cyclic N,N-di-lower alkyl carboxamides, such as, for example, N,N-dimethylformamide, N,N-dimethylacetamide, N-methyl-2-pyrrolidinone or sulphoxides, such as, for example, dimethyl sulphoxide and diethyl sulphoxide.

Preferred solvents are aromatic hydrocarbons having 7 to 9 carbon atoms, N, N-dimethylformamide, N, N-dimethylacetamide, N-methyl-2-pyrrolidinone, N-ethylpyrrolidinone, N-methylvalerolactam, N-methylcaprolactam, dimethyl sulphoxide, xylenes and anisole.

More preferred solvents are N,N-dimethylformamide, N-methyl-2-pyrrolidinone, dimethyl sulphoxide, xylenes and anisole.

The rearrangement can be carried out in the temperature range from 0 to 250° C., preferably in the range from 50 to 220° C., more preferably in the range from 80 to 190° C.

The reaction can be carried out at 0 to 200 bar, preferred pressures are in the range 1 to 50 bar.

The reduction of 3 to 4 in the third step advantageously takes place over hydrogenation catalysts in a hydrogen atmosphere. Suitable hydrogenation catalysts are, for example, elements of transition group 8 of the Periodic Table of the Elements. Particularly advantageous here are the elements nickel, palladium, platinum, rhodium, iridium, ruthenium and mixtures, compounds and alloys thereof. These catalysts can be used, for example, in finely divided form, applied to carriers or together with other metals or compounds thereof.

Advantageous carrier materials which may be mentioned are activated carbon, aluminum oxides, metal oxides, silica gels, zeolites, clays, clay granules, amorphous aluminum silicates, or other inorganic or polymeric carriers.

The hydrogen pressure during the hydrogenation reaction is in the range from 1 to 200 bar, preferably in the range from 1 to 100 bar, more preferably in the range from 5 to 50 bar.

The isolongifolanol (4) can be purified by customary methods, e.g. by distillation or crystallization.

The compound 4 prepared by the process according to the present invention is a fragrance and has complex odor properties. In addition to patchouli and wood notes, it has camphoraceous, ambergris and green notes. The incorporation into woody and spicy compositions is advantageous, and also an excellent recreation of natural patchouli oils is possible with 4.

A further part of the present invention relates to isolongifolenol of the structural formula:

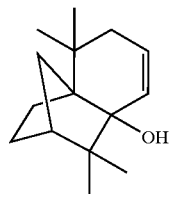

3

The compound according to the present invention, isolongifolenol (3), has notable and complex odor properties. In addition to the specifically requested patchouli and wood notes, it also has powerful earthy-camphoraceous and mossy-acrid aspects. The substance is distinguished by originality and natural character and by a very high intensity combined with a good staying power.

Surprisingly, isolongifolenol (3) differs significantly in terms of odor from isolongifolanol (4) by virtue of its very much earthier odor and the more intensive patchouli-typical character.

The isolongifolenol (3) according to the present invention can be purified by customary methods, e.g. by distillation or crystallization.

By using the isolongifolenol (3) according to the present invention, it is generally possible, even in a low concentration, to achieve fine, woody-earthy patchouli notes in the resulting fragrance compositions, the overall odor impression being remarkably harmonized. Incorporation into woody, chypre, oriental and spicy compositions is particularly effective. In a higher concentration, an excellent recreation of natural patchouli oils is possible.

The isolongifolenol (3) according to the present invention may be used here as an individual substance in a large number of products; it can be particularly advantageously combined with other fragrances to give new types of fragrance compositions.

Examples of fragrances with which the isolongifolenol (3) according to the present invention, and also the isolongifolanol (4) which can be prepared therefrom, can be advantageously combined are given, for example, in S. Arctander, Perfume and Flavor Materials, Vol. I and II, Montclair, N.J., 1969, published privately or K. Bauer, D. Garbe and H. Surburg, Common Fragrance and Flavor Materials, $3^{rd}$ Ed., Wiley-VCH, Weinheim 1997.

Individual examples which may be mentioned are: extracts from natural raw materials such as essential oils, concretes, absolutes, resins, resinoids, balsams, tinctures, such as, for example, ambergris tincture; amyris oil; angelica seed oil; angelica root oil; aniseed oil; valerian oil; basil oil; wood moss absolute; bay oil; mugwort oil; benzoin resin; bergamot oil; beeswax absolute; birch tar oil; bitter almond oil; savory oil; bucco leaf oil; cabreuva oil; cade oil; calmus oil; camphor oil; cananga oil; cardamom oil; cascarilla oil; cassia oil; cassia absolute; castoreum absolute; cedar leaf oil; cedarwood oil; cistus oil; citronella oil; lemon oil; copaiva balsam; copaiva balsam oil; coriander oil; costus root oil; cumin oil; cypress oil; davana oil; dill herb oil; dill seed oil; eau de brouts absolute; oakmoss absolute; elemi oil; estragon oil; eucalyptus citriodora oil; eucalyptus oil; fennel oil; spruce needle oil; galbanum oil; galbanum resin; geranium oil; grapefruit oil; guaiac wood oil; gurjun balsam; gurjun balsam oil; helichrysum absolute; helichrysum oil; ginger oil; iris root absolute; iris root oil; jasmine absolute; calamus oil; blue camomile oil; Roman camomile oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemongrass oil; lovage oil; distilled lime oil; pressed lime oil; linaloe oil; litsea cubeba oil; bayleaf oil; mace oil; marjoram oil; mandarin oil; massoi bark oil; mimosa absolute; musk seed oil; musk tincture; clary sage oil; nutmeg oil; myrrh absolute; myrrh oil; myrtle oil; clove leaf oil; clove flower oil; neroli oil; olibanum absolute; olibanum oil; opopanax oil; orange-flower absolute; orange oil; origanum oil; palmarosa oil; patchouli oil; perilla oil; Peruvian balsam oil; parsley leaf oil; parsley seed oil; petitgrain oil; peppermint oil; pepper oil; pimento oil; pine oil; pennyroyal oil; rose absolute; rosewood oil; rose oil; rosemary oil; Dalmation sage oil; Spanish sage oil; sandalwood oil; celery seed oil; spike lavender oil; Japanese anise oil; styrax oil; tagetes oil; fir needle oil; tea-tree oil; turpentine oil; thyme oil; Tolu balsam; tonka absolute; tuberose absolute; vanilla extract; violet leaf absolute; verbena oil; vetiver oil; juniper oil; wine lees oil; absinthe oil; wintergreen oil; ylang oil; hyssop oil; civet absolute; cinnamon leaf oil; cinnamon bark oil; and fractions thereof, or ingredients isolated therefrom;

individual fragrances from the group of hydrocarbons, such as, for example, 3-carene; α-pinene; β-pinene; α-terpinene; γ-terpinene; p-cymene; bisabolene; camphene; caryophyllene; cedrene; farnesene; limonene; longifolene; myrcene; ocimene; valencene; (E,Z)-1,3,5-undecatriene;

of aliphatic alcohols, such as, for example, hexanol; octanol; 3-octanol; 2,6-dimethylheptanol; 2-methylheptanol, 2-methyloctanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol; of aliphatic aldehydes and 1,4-dioxacycloalken-2-ones thereof, such as, for example, hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-5,9-undecadienal; heptanal diethyl acetal; 1,1-dimethoxy-2,2,5-trimethyl-4-hexene; citronellyl oxyacetaldehyde;

of aliphatic ketones and oximes thereof, such as, for example, 2-heptanone; 2-octanone; 3-octanone; 2-nonanone; 5-methyl-3-heptanone; 5-methyl-3-heptanone oxime; 2,4,4,7-tetramethyl-6-octen-3-one; of aliphatic sulphur-containing compounds, such as, for example, 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

of aliphatic nitriles, such as, for example, 2-nonenenitrile; 2-tridecenenitrile; 2,12-tridecadienenitrile; 3,7-dimethyl-2,6-octadienenitrile; 3,7-dimethyl-6-octenenitrile;

of aliphatic carboxylic acids and esters thereof, such as, for example, (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octynoate; methyl 2-nonynoate; allyl 2-isoamyloxyacetate; methyl 3,7-dimethyl-2,6-octadienoate;

of acyclic terpene alcohols, such as, for example, citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and formates, acetates, propionates, isobutyrates, butyrates, isovalerates, pentanoates, hexanoates, crotonates, tiglinates, 3-methyl-2-butenoates thereof;

of acyclic terpene aldehydes and ketones, such as, for example, geranial; neral; citronellal; 7-hydroxy-3,7-dimethyloctanal; 7-methoxy-3,7-dimethyloctanal; 2,6,10-trimethyl-9-undecenal; geranylacetone; and the dimethyl and diethyl acetals of geranial, neral, 7-hydroxy-3,7-dimethyloctanal;

of cyclic terpene alcohols, such as, for example, menthol; isopulegol; alpha-terpineol; terpineol-4; menthan-8-ol; menthan-1-ol; menthan-7-ol; borneol; isoborneol; linalool oxide; nopol; cedrol; ambrinol; vetiverol; guaiol; and formates, acetates, propionates, isobutyrates, butyrates, isovalerates, pentanoates, hexanoates, crotonates, tiglinates, 3-methyl-2-butenoates thereof;

of cyclic terpene aldehydes and ketones, such as, for example, menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-iron; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; nootkatone; dihydronootkatone; alpha-sinensal; beta-sinensal; acetylated cedarwood oil (methyl cedryl ketone);

of cyclic alcohols, such as, for example, 4-tert-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

of cycloaliphatic alcohols, such as, for example, alpha-3,3-trimethylcyclo-hexylmethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

of cyclic and cycloaliphatic ethers, such as, for example, cineol; cedryl methyl ether; cyclododecyl methyl ether; (ethoxymethoxy)cyclododecane; alpha-cedrene epoxide; 3a,6,6,9a-tetramethyidodecahydronaphtho[2,1-b]furan; 3a-ethyl-6,6,9a-trimethyldodecahydronaphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

of cyclic ketones, such as, for example, 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2- cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 6,7-dihydro-1,1,2,3,3-pentamethyl-4(5H)-indanone; 5-cyclohexadecen-1-one; 8-cyclohexadecen-1-one; 9-cycloheptadecen-1-one; cyclopentadecanone;

of cycloaliphatic aldehydes, such as, for example, 2,4-dimethyl-3-cyclo-hexenecarbaldehyde; 2-methyl-4-(2,2,6-trimethyl-cyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde;

of cycloaliphatic ketones, such as, for example, 1-(3,3-dimethylcyclohexyl)-4-penten-1-one; 1-(5,5-dimethyl-1-cyclohexen-1-yl)4-penten-1-one; 2,3,8,8-tetramethyl-1,2,3,4,5,6,7,8-octahydro-2-naphthalenyl methyl ketone; methyl-2,6,1 0-trimethyl-2,5,9-cyclododecatrienyl ketone; tert-butyl 2,4-dimethyl-3-cyclohexen-1-yl ketone;

of esters of cyclic alcohols, such as, for example, 2-tert-butylcyclohexyl acetate; 4-tert-butylcyclohexyl acetate; 2-tert-pentylcyclohexyl acetate; 4-tert-pentylcyclohexyl acetate; decahydro-2-naphthyl acetate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate; 4,7-methanooctahydro-5 or 6-indenyl acetate;

of esters of cycloaliphatic carboxylic acids, such as, for example, allyl 3-cyclohexyl-propionate; allyl cyclohexyloxyacetate; methyl dihydrojasmonate; methyl jasmonate; methyl 2-hexyl-3-oxocyclopentanecarboxylate; ethyl 2-ethyl-6,6-dimethyl-2-cyclo-hexenecarboxylate; ethyl 2,3,6,6-tetramethyl-2-cyclohexenecarboxylate; ethyl 2-methyl-1,3-dioxolan-2-acetate;

of aromatic hydrocarbons, such as, for example, styrene and diphenylmethane;

of araliphatic alcohols, such as, for example, benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

of esters of araliphatic alcohols and aliphatic carboxylic acids, such as, for example, benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate; of araliphatic ethers, such as, for example, 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

of aromatic and araliphatic aldehydes, such as, for example, benzaldehyde; phenylacetaldehyde; 3-phenylpropanal; hydratropaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert-butylphenyl)propanal; 3-(4-tert-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

of aromatic and araliphatic ketones, such as, for example, acetophenone; 4-methylacetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)ethanone; benzophenone; 1,1,2,3,3,6-hexamethyl-5-indanyl methyl ketone; 6-tert-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-aceto-naphthone;

of aromatic and araliphatic carboxylic acids and esters thereof, such as, for example, benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

of nitrogen-containing aromatic compounds, such as, for example, 2,4,6-trinitro-1,3-dimethyl-5-tert-butylbenzene; 3,5-dinitro-2,6-dimethyl-4-tert-butylacetophenone; cinnamonitrile; 5-phenyl-3-methyl-2-pentenenitrile; 5-phenyl-3-methylpentanenitrile; methylanthranilate; methyl N-methylanthranilate; Schiff bases of methyl anthranilate with 7-hydroxy-3,7-dimethyloctanal; 2-methyl-3-(4-tert-butylphenyl)propanal or 2,4-dimethyl-3-cyclohexenecarbaldehyde; 6-isopropylquinoline; 6-isobutylquinoline; 6-sec-butylquinoline; indole; skatole; 2-methoxy-3-isopropylpyrazine; 2-isobutyl-3-methoxypyrazine;

of phenols, phenyl ethers and phenyl esters, such as, for example, estragole; anethole; eugenole; eugenyl methyl ether; isoeugenole; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenylacetate;

of heterocyclic compounds, such as, for example, 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

of lactones, such as, for example, 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolde; 11-oxa-1,16-hexadecanolide; 12-oxa-1,16-hexa-decanolide; ethylene 1,12-dodecanedioate; ethylene 1,13-tridecanedioate; coumarin; 2,3-dihydrocoumarin; octahydrocoumarin.

The perfume oils comprising the isolongifolenol according to the present invention can be used in liquid form, neat or diluted with a solvent for perfumings. Suitable solvents for this purpose are, for example, ethanol, isopropanol, diethylene glycol monoethyl ether, glycerol, propylene glycol, 1,2-butylene glycol, dipropylene glycol, diethyl phthalate, triethyl citrate, isopropyl myristate etc.

In addition, the perfume oils comprising the isolongifolenol (3) according to the present invention can be adsorbed on a carrier which serves both to distribute the fragrances finely within the product and to release them in a controlled manner during use. Such carriers can be porous inorganic materials such as light sulphate, silica gels, zeolites, gypsums, clays, clay granules, gas concrete etc. or organic materials such as woods and cellulose-based substances.

The perfume oils comprising the isolongifolenol according to the present invention can also be microencapsulated, spray dried, in the form of inclusion complexes or in the form of extrusion products and be added in this form to the product to be perfumed.

The properties of the perfume oils modified in this way can optionally be further optimized by "coating" with suitable materials with regard to a more targeted fragrance release, for which purpose preference is given to using wax-like polymers, such as, for example, polyvinyl alcohol.

The microencapsulation of the perfume oils can, for example, be carried out by the "coacervation method" using capsule materials made from, for example, polyurethane-like substances or soft gelatin. The spray-dried perfume oils can, for example, be prepared by spray drying an emulsion or dispersion comprising the perfume oil, where the carriers used can be modified starches, proteins, dextrin and vegetable gums. Inclusion complexes can be prepared, for example, by introducing dispersions of the perfume oil and cyclodextrins or urea derivatives into a suitable solvent, e.g. water. Extrusion products can be obtained by melting the perfume oils with a suitable wax-like substance and by extrusion with subsequent solidification, optionally in a suitable solvent, e.g. isopropanol.

In the fragrance compositions according to the present invention, the amount of the isolongifolenol (3) according to the present invention used is 0.05 to 80% by weight, preferably 0.5 to 50% by weight, based on the total perfume oil.

The perfume oils comprising the isolongifolenol according to the present invention can be used in concentrated form, in solutions or in the above-described modified form for the preparation of, for example, perfume extracts, eaux de parfum, eaux de toilettes, aftershaves, eaux de colognes, pre-shave products, splash colognes and perfumed freshening wipes, and the perfuming of acidic, alkaline and neutral cleaners, such as, for example, floor cleaners, window cleaners, dishwashing detergents, bath and sanitary cleaners, scouring milk, solid and liquid WC cleaners, pulverulent and foam carpet cleaners, liquid laundry detergents, pulverulent laundry detergents, laundry pretreatment agents, such as bleaches, soaking agents and stain removers, fabric softeners, washing soaps, washing tablets, disinfectants, surface disinfectants, and of air fresheners in liquid or gel form or deposited on a solid carrier, aerosol sprays, waxes and polishes, such as furniture polishes, floor waxes, shoe creams, and bodycare compositions, such as, for example, solid and liquid soaps, shower gels, shampoos, shaving soaps, shaving foams, bath oils, cosmetic emulsions of the oil-in-water, water-in-oil and water-in-oil-in-water type, such as, for example, skin creams and lotions, face creams and lotions, sunscreen creams and lotions, aftersun creams and lotions, hand creams and lotions, foot creams and lotions, depilatory creams and lotions, aftershave creams and lotions, tanning creams and lotions, haircare products, such as, for example, hairsprays, hair gels, hairsetting lotions, hair rinses, permanent and semipermanent hair colorants, hair-shaping compositions, such as cold waves and hair-smoothing compositions, hair tonics, hair creams and lotions, deodorants and antiperspirants, such as, for example, underarm sprays, roll-ons, deodorant sticks, deodorant creams, products in decorative cosmetics, such as, for example, eyeshadows, nail varnishes, foundations, lipsticks, mascara, and of candles, lamp oils, joss-sticks, insecticides, repellents, propellants.

The incorporation of the isolongifolenol according to the present invention into perfume oils for shampoos and shower gels proved to be particularly successful. Another major use of the isolongifolenol according to the present invention is in the perfuming of soaps and detergents because of its stability in the alkaline range. In the case of the use in detergent perfumings, the isolongifolenol according to the present invention is distinguished by its naturalness and high substantivity, i.e. its good adhesion to the washed fibers. This also applies to isolongifolanol.

In addition to its stability in media (in acidic, basic and oxidative media), the compound according to the present invention isolongifolenol has the property of intensifying the odor impression of other compounds, i.e. it is an "enhancer" or "booster".

An additionally noteworthy property of isolongifolenol to be mentioned is the odor-masking or odor-concealing effect which can be achieved with this compound, an effect which is of interest particularly in the bodycare and haircare products sector. Similar effects can be achieved with iso-longifolanol.

EXAMPLES

The following examples illustrate the invention:

The percentages given in the examples refer to percentages by weight. Starting from isolongifolene (GC purity: about 78%), the isolongifolene epoxide (2) was obtained in a GC purity of about 75% in accordance with details in the literature (see above) using peracetic acid oxidation, which epoxide is used in the examples below.

Example 1

In a protective gas atmosphere, 333 g of isolongifolene epoxide (1.1 mol based on the GC content of epoxide) were dissolved in 500 g of dimethyl sulphoxide. 123 g (1.1 mol) of potassium tert-butoxide were added thereto, and the mixture was heated at 95° C. for 12 hours. When the reaction had finished (complete conversion), the reaction mixture was added to 400 ml of water, the phases were separated and the aqueous phase was extracted four times with n-heptane. The combined organic phases were washed with water and dried with sodium sulphate. The oil which remained following removal of the solvent was used for the further purification.

The residue was fractionated over a column packed with steel helices or glass rings, giving 242 g of isolongifolenol at 100–105° C./1 mbar with a GC purity of >93%.

The substance can be further purified by recrystallization from n-hexane or ethanol. Melting point: 37–38° C. (n-hexane).

¹H-NMR (400 MHz, CDCl₃): δ (ppm)=0.92 (q, J=0.5 Hz, 3H), 0.95 (m, 6H), 0.98 (m, 3H), 1.16 (s, 1H), 1.25 (dd, J=1.8, 10.0 Hz, 1H), 1.39 (m, 2H), 1.57 (ddt,J=1.9,2.8, 10.0 Hz, 1H), 1.64 (m, 1H), 1.74 (ddd, J=0.9, 6.0, 17.6 Hz, 1H), 1.81 (m, 2H), 2.01 (dsept, J=0.9, 17.6 Hz, 1H), 5.58 (ddd, J=1.9, 6.0, 10.3 Hz, 1H), 5.67 (ddt, J=0.9, 2.8, 10.3 Hz, 1H).
¹³C-NMR (100 MHz, CDCl₃): δ (ppm)=20.61, 21.73, 24.37, 25.29, 26.80, 27.53, 32.10, 35.90, 39.02, 44.08, 47.77, 58.24, 77.82, 124.43, 130.88.

Example 2

In a protective gas atmosphere, 320 g of isolongifolene epoxide (1.06 mol based on the GC content of epoxide) were dissolved in 300 g of N-methyl-2-pyrrolidinone. 88.5 g (1.3 mol) of sodium ethoxide were added thereto, and the mixture was heated at 160° C. for 10 hours. When the reaction was complete (conversion: 95%), the solvent was largely distilled off under reduced pressure and the residue was dispersed on 300 ml of water and 150 g of toluene. After the aqueous phase had been separated off, it was extracted twice more with toluene, and the combined organic phases were washed with water. The product phase was dried with sodium sulphate and concentrated by evaporation. Further purification of the crude product can be carried out as in Example 1. Distillation gave 215 g of isolongifolenol (GC purity: 92%).

Example 3

In a protective gas atmosphere, 333 g of isolongifolene epoxide (1.1 mol based on the GC content of epoxide) were dissolved in 500 g of N,N-dimethylformamide. 97 g (1.8 mol) of sodium methoxide were added thereto, and the mixture was heated at 180° C. for 18 hours. When the reaction was complete (conversion: 93%), the work-up was carried out as described in Example 2. Distillation gave 213 g of isolongifolenol (GC purity: >94%).

Example 4

In a protective gas atmosphere, 333 g of isolongifolene epoxide (1.1 mol based on the GC content of epoxide) were dissolved in 500 g of anisole. 141 g (1.25 mol) of potassium tert-butoxide were added thereto, and the mixture was heated at 140° C. for 16 hours. When the reaction was complete (conversion: 92%), the reaction mixture was added to 250 ml of water, the phases were separated and the aqueous phase was extracted twice with toluene. The combined organic phases were washed with water, dried with sodium sulphate and concentrated by evaporation. Distillation of the residue gave 220 g of isolongifolenol (GC purity: 94%).

Example 5

In a protective gas atmosphere, 73.2 g of diethylamine (1 mol) were introduced into 300 ml of diethyl ether and cooled to 0° C. using an ice bath. Over the course of 30 minutes, 42 ml of a 2.5 M solution of n-butyllithium in hexane were added dropwise thereto. After 10 minutes, 272 g of isolongifolene epoxide (0.9 mol based on the GC content of epoxide) in 300 ml of diethyl ether were added dropwise over the course of one hour. After the addition was complete, the cooling bath was removed and the reaction mixture was refluxed for 16 hours. The cooled reaction mixture was poured onto 500 g of ice. Following phase separation, the aqueous phase was extracted three times with diethyl ether. The combined organic phases were washed successively with 1 N hydrochloric acid, bicarbonate solution and water. After drying with sodium sulphate, the solvent was removed. Distillation of the residue gave 155 g of isolongifolenol (GC purity: 94%).

Example 6

In a protective gas atmosphere, 333 g of isolongifolene epoxide (1.1 mol based on the GC content of epoxide) and 11.6 g (0.1 mol) of trilithium phosphate were combined. The mixture was heated at 160° C. for 4 hours. The cooled reaction mixture (conversion: 84%) was added to 100 ml of water and 150 ml of diethyl ether, the phases were separated and the aqueous phase was extracted twice with diethyl ether. The combined organic phases were washed with water, dried with sodium sulphate and freed from the solvent. Distillative purification of the residue gave 138 g of isolongifolenol (GC purity: 95%).

Example 7

In a protective gas atmosphere, 7 g of lithium were dissolved in 300 ml of anhydrous ethylenediamine. At 110° C., 151 g of isolongifolene epoxide (0.5 mol based on the GC content of epoxide) were then slowly added dropwise and the mixture was stirred for a further 3 hours at this temperature. 200 ml of water were carefully added to the cooled reaction mixture, the phases were separated and the aqueous phase was extracted twice with diethyl ether. The combined organic phases were washed with water, dried with sodium sulphate and concentrated by evaporation. Distillative purification of the residue gave 78 g of isolongifolenol (GC purity: >92%).

Example 8

In a protective gas atmosphere, 333 g of isolongifolene epoxide (1.1 mol based on the GC content of epoxide) were dissolved in 500 g of p-xylene. 132 g (1.18 mol) of potassium tert-butoxide were added thereto, and the mixture was heated at the reflux temperature for 24 hours. When the reaction was complete (conversion: 92%), the reaction mixture was added to 200 ml of water, the phases were separated and the aqueous phase was extracted twice with toluene. The combined organic phases were washed with water, dried with sodium sulphate and concentrated by evaporation. Distillation of the residue gave 216 g of isolongifolenol (GC purity: 94%).

Example 9

Using the present example, the recreation of a perfume oil with a natural patchouli character can be illustrated.

TABLE 1

| Ingredients | Parts by weight |
| --- | --- |
| 1. Isobornyl acetate | 5.5 |
| 2. Borneol L | 25.0 |
| 3. Camphor | 15.0 |
| 4. Davana oil f. perf. | 1.0 |
| 5. Nopol | 95.0 |
| 6. Dimethylbenzylcarbinyl acetate | 5.5 |
| 7. Terpineol, pure | 11.0 |
| 8. Palmarosa oil | 6.0 |
| 9. Caryophyllene rect. | 20.0 |
| 10. Butylcyclohexanol para-tert | 32.5 |
| 11. Cedarwood oil, Florida | 25.0 |
| 12. Palisandin (H&R) | 162.0 |
| 13. Vetiver oil, Java | 5.5 |

TABLE 1-continued

| Ingredients | Parts by weight |
| --- | --- |
| 14. Gurjun balsam, Siam | 102.5 |
| 15. Sandel 80 (H&R) | 7.5 |
| 16. Fixative, wood | 35.0 |
| 17. Elemi resin EE | 36.5 |
| 18. Opoponax resin, dewaxed | 5.0 |
| 19. Karanal (Quest) | 2.5 |
| 20. Globalid 100% (H&R) | 2.0 |
| 21. Isolongifolenol | 400.0 |

Example 10

In a hydrogenation apparatus, 200 g of isolongifolenol are introduced into 200 g of ethanol, 1% of hydrogenation catalyst is added (e.g. 5% palladium on activated carbon) and, at a hydrogen pressure of 10 bar, the mixture is hydrogenated until no further hydrogen absorption can be registered. Following removal of the catalyst and the solvent, the reaction product was analyzed by gas chromatography. The conversion of 3 was >98%. 197 g of crude hydrogenation product were isolated. To purify the isolongifolanol 4, the crude hydrogenation product was recrystallized from ethanol or hexane or petroleum ether.

The resulting isolongifolanol has a purity of >99% and has a melting point of 67° C. (n-hexane).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of isolongifolanol (4), comprising the following steps:

a) epoxidizing isolongifolene (1) to give isolongifolene oxide (2),
    b) rearranging isolongifolene oxide (2) in the presence of a base to give isolongifolenol (3) and
    c) reducing isolongifolenol (3) to give isolongifolanol (4).

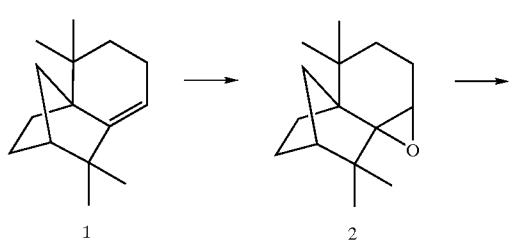

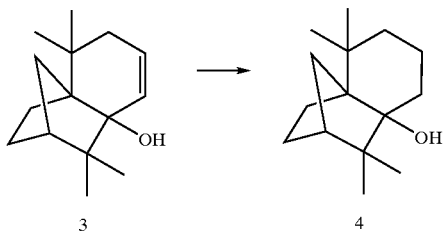

2. A process according to claim 1, wherein said base is alkali metal, alkaline earth metal or light metal alkoxides or alkali metal, alkaline earth metal or light metal amides.

3. A process according to claim 2, wherein said base is sodium methoxide, sodium ethoxide, sodium isopropoxide, sodium tert-butoxide, potassium methoxide, potassium ethoxide, potassium isopropoxide, potassium tert-butoxide, lithium methoxide, lithium ethoxide, lithium isopropoxide or lithium tert-butoxide.

4. A process according to claim 1, wherein process step b) is carried out in the temperature range from 0 to 250° C.

5. Isolongifolenol of the formula

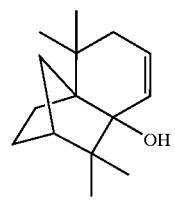

6. A fragrance composition comprising isolongifolenol of the formula

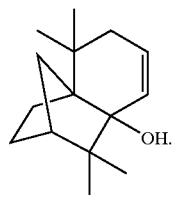

7. An aroma substance comprising isolongifolenol of the formula

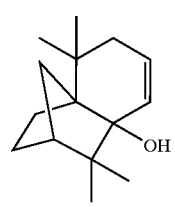

* * * * *